US008067405B2

(12) United States Patent
Klimko et al.

(10) Patent No.: US 8,067,405 B2
(45) Date of Patent: *Nov. 29, 2011

(54) SUPEROXIDE DISMUTASE MIMICS FOR THE TREATMENT OF OCULAR DISORDERS AND DISEASES

(75) Inventors: Peter G. Klimko, Fort Worth, TX (US); Robert J. Collier, Jr., Arlington, TX (US); Mark R. Hellberg, Arlington, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/730,820

(22) Filed: Mar. 24, 2010

(65) Prior Publication Data

US 2010/0179117 A1   Jul. 15, 2010

Related U.S. Application Data

(63) Continuation of application No. 10/534,796, filed as application No. PCT/US03/38677 on Dec. 5, 2003, now Pat. No. 7,754,706.

(60) Provisional application No. 60/431,414, filed on Dec. 6, 2002.

(51) Int. Cl.
*A61K 31/555* (2006.01)
(52) U.S. Cl. ......................... 514/185; 514/184; 514/912
(58) Field of Classification Search .................. 514/184, 514/185, 912
See application file for complete search history.

(56) References Cited

U.S. PATENT DOCUMENTS

| 5,075,116 | A | 12/1991 | LaHaye et al. | |
|---|---|---|---|---|
| 5,510,383 | A * | 4/1996 | Bishop et al. ................. | 514/530 |
| 5,696,109 | A | 12/1997 | Malfroy-Camine et al. | |
| 5,994,339 | A | 11/1999 | Crapo et al. | |
| 6,046,188 | A | 4/2000 | Malfroy-Camine et al. | |
| 6,127,356 | A | 10/2000 | Crapo et al. | |
| 6,177,419 | B1 | 1/2001 | Campbell et al. | |
| 6,180,620 | B1 | 1/2001 | Salvemini | |
| 6,214,817 | B1 | 4/2001 | Riley et al. | |
| 6,541,490 | B1 | 4/2003 | Campbell et al. | |
| 2006/0035880 | A1 | 2/2006 | Klimko et al. | |

FOREIGN PATENT DOCUMENTS

| WO | 9858636 A1 | 12/1998 |
|---|---|---|
| WO | 9923097 A1 | 5/1999 |
| WO | 0007584 A2 | 2/2000 |
| WO | 0019993 A2 | 4/2000 |
| WO | 0072893 A2 | 12/2000 |
| WO | 2004052283 A2 | 6/2004 |

OTHER PUBLICATIONS

Allikmets R, et al., "Mutation of the Stargardt Disease Gene (ABCR) in Age-Related Macular Degeneration", Science, 277:1805-1807 (1997). Listed as "Dean" in application.

Baker et. al., "Synthetic Combined Superoxide Dismutase/Catalase Mimetics Are Protective as a Delayed Treatment in a Rat Stroke Model: A Key Role for Reactive Oxygen Species in Ischemic Brain", J. Pharmacol. Exp. Ther., vol. 284:215-221, 1998.
Bazan; "Cell survival matters: docosahexaenoic acid signaling, neuroprotection and photoreceptors"; Trends in Neurosciences; vol. 29; No. 5; pp. 263-271; May 2006.
Ben-Shabat et al., "Fluorescent Pigments of the Retinal Pigment Epithelium and Age-Related Macular Degeneration", Bioorganic & Medicinal Chemistry Letters, 11:1533-1540, 2001. Listed as "Nakanishi" in application.
Brownlee, M., "Biochemistry and Molecular Cell Biology of Diabetic Complications", Nature, vol. 414:813-820, 2001.
Coppey, et al., "Effect of M40403 Treatment of Diabetic Rats on Endoneurial Blood Flow, Motor Nerve Conduction Velocity and Vascular Function of Epineural Arterioles of the Siatic Nerve," British Journal of Pharmacology, vol. 134:21-9, 2001 (M40403).
Delcourt, et al., "Associations of Antioxidant Enzymes with Cataract and Age-related Macular Degeneration", Ophthalmology, Feb. 1999, pp. 215-221, vol. 106, No. 2.
De La Paz, et al., "Red Blood Cell Antioxidant Enzymes in Age-related Macular Degeneration", British Journal of Ophthalmology, 1996, pp. 445-450, vol. 80.
Doctrow et. al., "Salen-Manganese Complexes as Catalytic Scavengers of Hydrogen Peroxide and Cytoprotective Agents: Structure-Activity Relationship Studies", J. Med. Chem., 45:4549-4558 (2002).
Gürler, et al., "The Role of Oxidative Stress in Diabetic Retinopathy" Eye, vol. 14:730-735, 2000.
Guzik, et al., "Mechanisms of Increased Vascular Superoxide Production in Human Diabetes Mellitus" Circulation, vol. 105:1656-62, 2002.
Kimura K et al., "Genetic Association of Manganese Superoxide Dismutase With Exudative Age-related Macular Degeneration", American Journal of Ophthalmology, 130(6):769-773 (2000). Listed as "Isashiki" in the application.
Mata NL et al., "Biosynthesis of a major lipofuscin fluorophore in mice and humans with ABCR-mediated retinal and macular degeneration", Proc. Natl. Acad. Sci. USA, 97(13):7154-7159 (2000). Listed as "Travis" in the application.
Melov et. al., "Lipespan Extension and Rescue of Spongiform Encephalopathy in Superoxide Dismutase 2 Nullizygous Mice Treated with Superoxide Dismutase-Catalase Mimetics", J. Neurosci., vol. 21:8348-8353, 2001.
Parish et al. (Nakanishi), "Isolation and one-step preparation of A2E and iso-A2E, fluorophores from human retinal pigment epithelium", Proc. Natl. Acad. Sci. USA, 95:14609-14613, 1998.
Piganelli, et al., "A Metalloporphyrin-Based Superoxide Dismutase Mimic Inhibits Adoptive Transfer of Autoimmune Diabetes by a Diabetogenic T-cell Clone," Diabetes, vol. 51:347-55, 2002.
Salvemini D, et. al., "A Nonpeptidyl Mimic of Superoxide Dismutase with Therapeutic Activity in Rats", Science, vol. 286:304-306, 1999.
Salvemini, et al., "M40403 Superoxide Dismutase Mimetic", Drugs of the Future, 25(10):1027-1033, 2000.
Shamsi and Boulton, "Inhibition of RPE Lysosomal and Antioxidant Activity by the Age Pigment Lipofuscin", Invest. Ophthalmol. Vis. Sci., vol. 42:3041-3046, 2001.

(Continued)

*Primary Examiner* — Zohreh Fay
(74) *Attorney, Agent, or Firm* — Jason J. Derry

(57) ABSTRACT

The use of SOD mimics, particularly Mn(III) salen SOD mimics, for the treatment of AMD, DR, and retinal edema is disclosed.

5 Claims, No Drawings

OTHER PUBLICATIONS

Shurtz-Swirski et al., "Involvement of Peripheral Polymorphonuclear Leukocytes in Oxidative Stress and Inflammation in Type 2 Diabetic Patients," Diabetes Care, vol. 24:104-110, 2001.

Wang et. al., "Tempol, a Superoxide Dismutase Mimic, Ameliorates Light-Induced Retinal Degeneration", Res. Commun. Mol. Pathol. Pharmacol., 89(3):291-305, 1995.

Wassell et al., "The Photoeactivity of the Retinal Age Pigment Lipofusin", J. Biol. Chem., 274:23828-23832, 1999.

Wihlmark et. al., "Lipofuscin Accumulation in Cultured Retinal Pigment Epithelial Cells Causes Enhanced Sensitivity to Blue Light Irradiation", Free Radical Biol. Med., 22:1229-1234, 1997.

Winkler, et. al., "Oxidative damage and age-related macular degeneration", Mol. Vision, vol. 5:32, 1999.

European Search Report from corresponding European Patent application publication No. 0739218 dated Oct. 30, 1996.

* cited by examiner

SUPEROXIDE DISMUTASE MIMICS FOR THE TREATMENT OF OCULAR DISORDERS AND DISEASES

The present application is a continuation of U.S. patent application Ser. No. 10/534,796 filed May 12, 2005 (now allowed), which is the National Stage of International Application Serial No. PCT/US2003/038677 filed Dec. 5, 2003, which claims benefit U.S. Provisional Application Ser. No. 60/431,414 filed Dec. 6, 2002.

The present invention relates to mimics of the enzyme superoxide dismutase for the treatment of the exudative and non-exudative forms of age-related macular degeneration, diabetic retinopathy, and retinal edema.

BACKGROUND OF THE INVENTION

Age-related macular degeneration (AMD) is the most common cause of vision impairment in the elderly population in western countries. The exudative or "wet" form of AMD is characterized by excessive neovascularization of the choroid, leading to retinal detachment and vision loss. The non-exudative or "dry" form is characterized by the accumulation of cellular debris called drusen in Bruch's membrane below the retinal pigmented epithelium (RPE). Exudative AMD, which occurs in a minority of patients with AMD, but is the more aggressive form of the disease, can be treated with limited success by laser photocoagulation therapy or photodynamic therapy. The latter procedure involves dosing of the affected area with a compound which, when irradiated with the appropriate wavelength of light, generates a reactive intermediate that destroys surrounding blood vessels. Currently there is no accepted therapy for the treatment of non-exudative AMD.

The visual cycle begins in photoreceptor cells with the absorption of a photon by an opsin-bound Schiff base of 11-cis retinal, which isomerizes to the corresponding all-trans retinal derivative. Release of the all-trans retinal from opsin is followed by condensation with phosphatidylethanolamine to form the new Schiff base NRPE (for N-Retinyl Phosphatidyl Ethanolamine). The NRPE so formed is transported across the photoreceptor cell outer membrane, where it is hydrolyzed to all-trans retinal. Enzymatic reduction to all-trans retinol is followed by transport into the RPE cell, where the compound is enzymatically isomerized to 11-cis retinol and oxidized to 11-cis retinal. This compound is transported back to the photoreceptor cell, where it forms an opsin-bound Schiff base to complete the cycle.

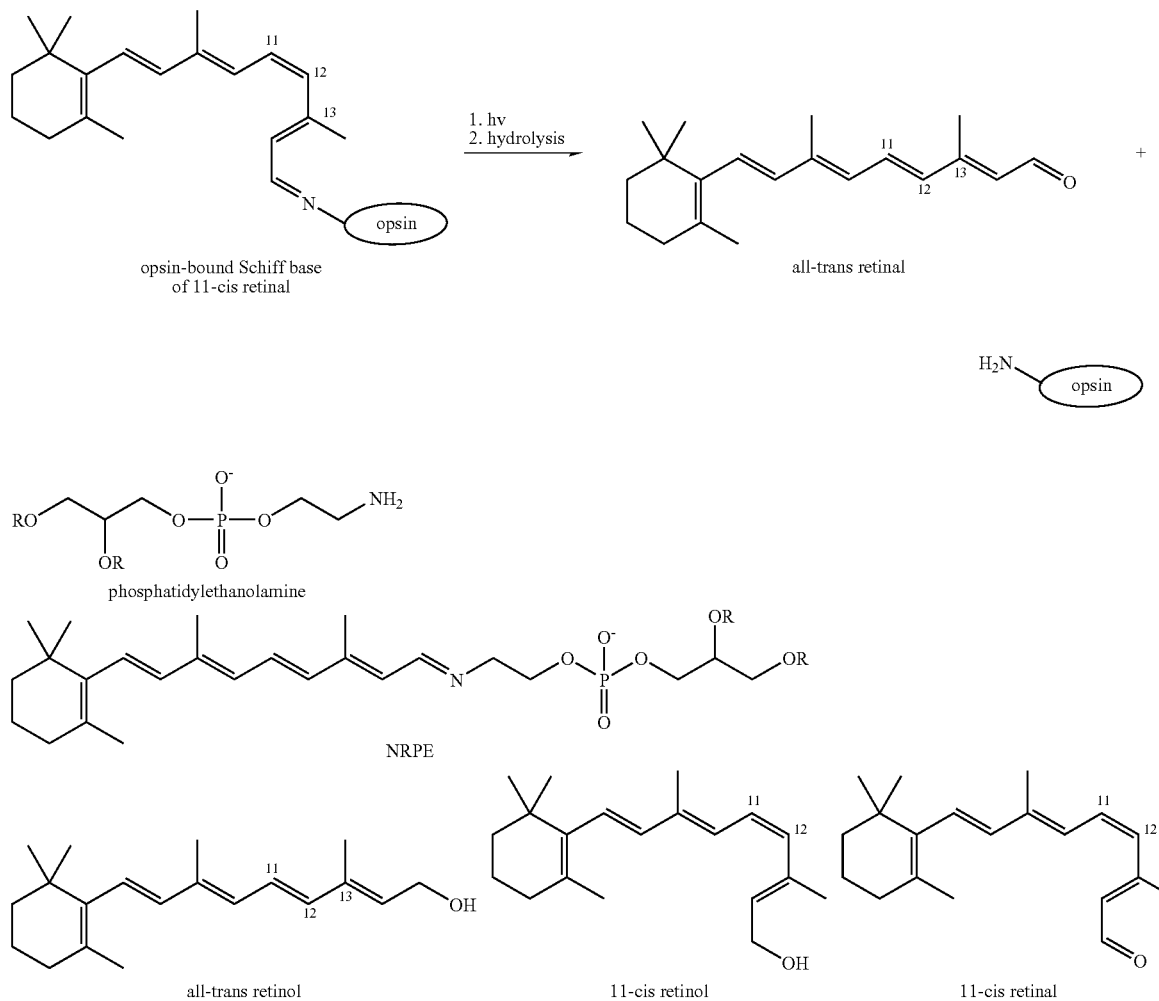

Besides helping to complete the visual cycle by recycling retinal, an important function of RPE cells is to support the continuous remodeling of retinal photoreceptors by phagocytosing their discarded outer segments and digesting them in RPE cell lysosomes. With age occurs the accumulation of a non-digestible pigment called lipofuscin in the lysosomes (the appearance of drusen is thought to correspond to lipofuscin accumulation). Lipofuscin absorbs light in the blue part of the spectrum and fluoresces in the yellow part of the spectrum. This fluorescence transfers energy to nearby oxygen, which becomes transformed into reactive oxygen species (ROS), such as superoxide ion. These ROS oxidize lysosomal membrane phospholipids, destroying membrane integrity. With membrane integrity breached the toxic contents of the lysosome leach into the cytosol, leading to RPE cell death. Without their supporting RPE cells retinal photoreceptors cannot participate in the visual transduction system, thus leading to blindness (for a review, see Winkler, et. al., Mol. Vision, Vol. 5:32, 1999, online journal; http://www-.molvis.org/molvis/v5/p32; CA 132:235390).

Nakanishi and co-workers have elucidated the structure of and chemically synthesized the major fluorescent constituent of lipofuscin, called A2E (Nakanishi et. al., Proc. Natl. Acad. Sci. USA, Vol. 95:14609-14613, 1998, and references therein). This compound is thought to result biosynthetically from isomerization of electrophilic NRPE to the nucleophilic enamine 1, followed by condensation with another molecule of all-trans retinal to form azatriene 2, electrocyclic ring closure to dihydropyridine 3, autoxidation to the N-(2-hydroxyethyl)pyridinium species A2PE, and enzymatic hydrolysis of the phosphate ester by the enzyme phospholipase D to afford A2E. The chemical structure of A2E-a molecule with two large hydrophobic "tails" and a charged polar "head"-suggests a detergent-like propensity to breach cell membranes. Along with its photooxidative capabilities, this may form an important component of the compound's toxic effects on RPE cells (for a review, see: Nakanishi et. al., Bioorganic and Medicinal Chemistry Letters, Vol. 11:1533-1540, 2001).

NRPE

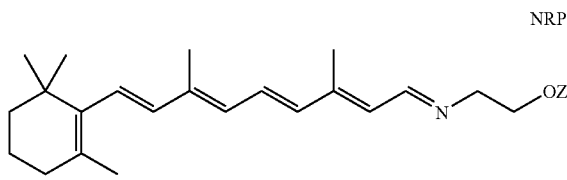

1

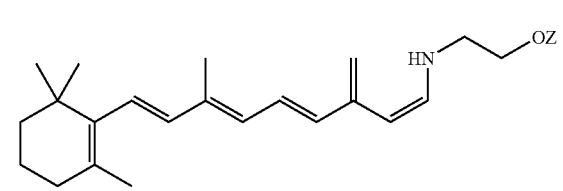

-continued

2

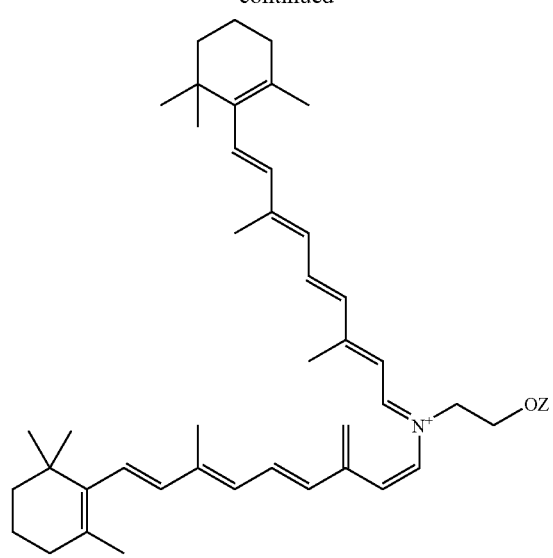

3

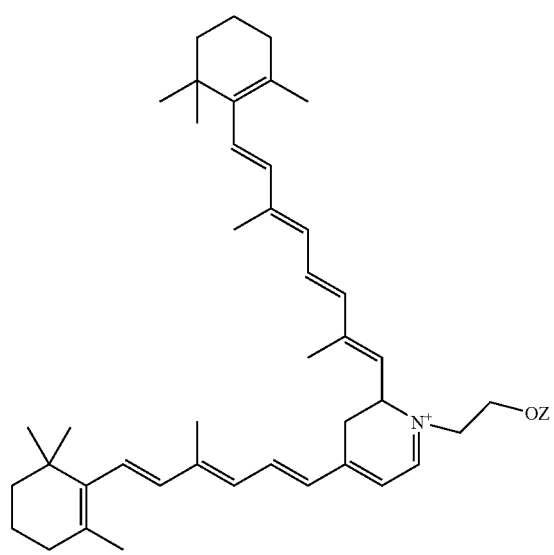

A2PE

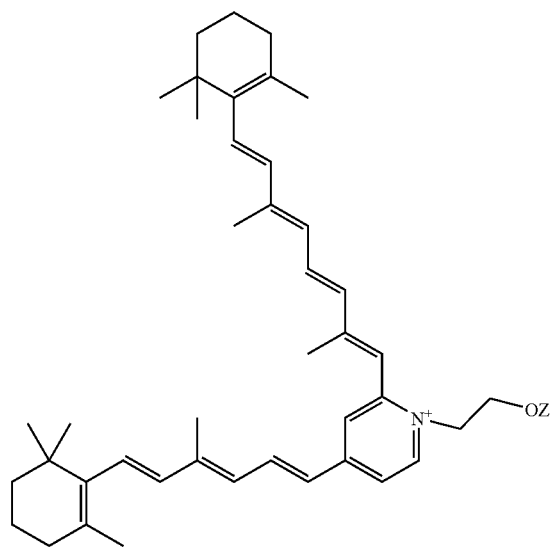

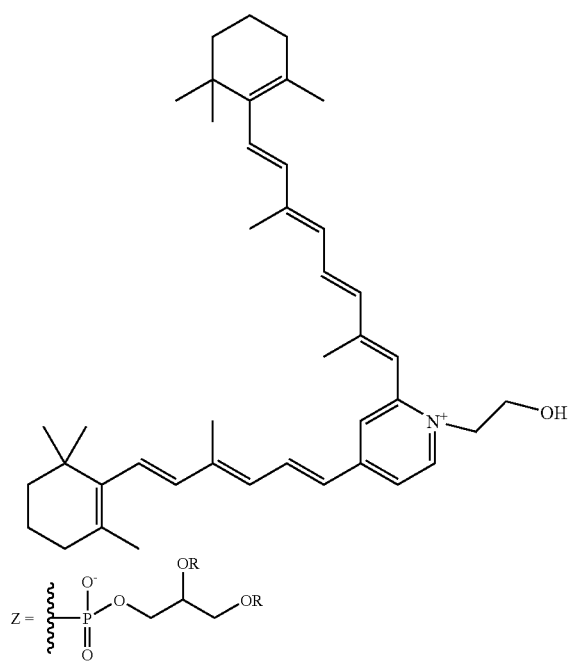

A2E

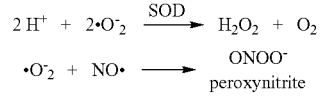

The key role of defective transport of all-trans retinal out of the photoreceptor cell in the AMD disease process has been highlighted by the discovery that a genetic mutation that when homozygously present leads to a rare rapid macular degeneration called Stargardt's Disease may be associated, when heterozygously expressed, with non-exudative AMD (Dean et. al., Science, Vol. 277:1805-1807, 1997). The gene is called the ABCR gene (for ATP Binding Cassette Transporter Retina), whose protein product (also called rim protein) utilizes the energy released upon ATP hydrolysis to transport molecules across cell membranes. It is thought that the transporter's substrate is the Schiff base NRPE mentioned above. Absent sufficient functional transporter protein, the substrate NRPE accumulates in the photoreceptor cell instead of being shuttled out for reduction to retinol. Condensation with a molecule of all trans-retinal liberated from opsin and further reaction as mentioned above produces A2E. The A2E is ingested by RPE cells with the rest of the photoreceptor cell outer segment, where it accumulates in the lysosome. Supporting this hypothesis is the disclosure by Travis et. al. that A2E accumulation in RPE cells occurs much more rapidly in mice that are homozygously mutant in the ABCR gene, as compared to normal controls (Travis et. al., Proc. Natl. Acad. Sci. USA, Vol. 97:7154-7159, 2000).

Several studies have concluded that exposure of lipofuscin to light and oxygen under conditions mimicking those present in the retina leads to cell membrane peroxidation and cell death. Wihlmark et. al. disclosed that blue light irradiation of RPE cells with lipofuscin-loaded lysosomes increased cell membrane peroxidation and decreased cell viability, as compared to controls irradiated in the absence of lipofuscin (Wihlmark et. al., Free Radical Biol. Med. Vol. 22:1229-1234, 1997). Boulton and Shamsi have disclosed that dosing of cultured RPE cells with lipofuscin and exposing them to light decreased cell viability by over 40% after 24 hours and decreased lysosomal enzymatic and antioxidant activity, including that of superoxide dismutase (SOD) (Boulton and Shamsi, Invest. Ophthalmol. Vis. Sci., Vol. 42:3041-3046, 2001).

From this and other evidence, it is clear that certain defects in the body's natural defense mechanisms for dealing with toxic by-products of oxidative metabolism may play an important role in the development of AMD. One important component of this defense system is the SOD enzyme family. These enzymes contain a low valent metal (either $Mn^{II}$ or a $Cu^I/Zn^I$ binuclear linkage) which catalyze the disproportionation of the highly reactive superoxide radical anion to the less toxic entities $O_2$ and $H_2O_2$. If not quenched the superoxide anion can (via its protonated form) abstract hydrogens from the allylic sites of fatty acids, leading to membrane damage. Additionally superoxide anion can react with NO to produce peroxynitrite, a potent oxidizing agent that is believed to be an important player in the untoward biological effects of excessive NO production.

$$2\,H^+ + 2 \cdot O_2^- \xrightarrow{SOD} H_2O_2 + O_2$$

$$\cdot O_2^- + NO \cdot \longrightarrow \underset{\text{peroxynitrite}}{ONOO^-}$$

The potential importance of SOD in enhancing RPE cell viability is suggested by the disclosure of Boulton et. al, who have reported that the damaging effects caused by irradiation of lipid membranes, proteins, and enzymes in the presence of lipofuscin can be significantly reduced by the addition of SOD (Boulton et. al., J. Biol. Chem., Vol. 274:23828-23832, 1999). Even with respect to exudative AMD, a recent study in Japanese subjects disclosed a significant correlation between this form of the disease and a mutation in the SOD gene, corresponding to a valine/alanine substitution in the targeting sequence of the enzyme (Isashiki et. al., Am. J. Ophthalmol., Vol. 130:769-773, 2000). Thus, enhancing SOD function may be a viable target for preventing the development of both the exudative and non-exudative forms of AMD.

Oxidative stress also contributes to diabetes induced vascular and neural dysfunction. All forms of diabetes result in the development of diabetes specific microvascular pathology of the retina, renal glomerulus and peripheral nerve (M. Brownlee, "Biochemistry and Molecular Cell Biology of Diabetic Complications", Nature, Vol. 414:813-820, 2001). A prime source of the oxidative insult associated with diabetes is elevated levels of superoxide. Release of superoxide was detected in human blood vessels isolated from, patients with diabetes (Guzik, et al., "Mechanisms of Increased Vascular Superoxide Production in Human Diabetes Mellitus" Circulation, Vol. 105:1656-62, 2002). Sources of superoxide include the vascular tissues and polymorphonuclear leukocytes (Shurtz-Swirski et al., "Involvement of Peripheral Polymorphonuclear Leukocytes in Oxidative Stress and Inflammation in Type 2 Diabetic Patients," Diabetes Care, Vol. 24:104-110, 2001). Superoxide Dismutase mimics have been shown to delay the onset of diabetes (AEOL10113—Piganelli, et al., "A Metalloporphyrin-Based Superoxide Dismutase Mimic Inhibits Adoptive Transfer of Autoimmune Diabetes by a Diabetogenic T-cell Clone," Diabetes, Vol. 51:347-55, 2002.) in a cloned cell and prevented vascular and neural dysfunction in diabetic rats (M40403—Coppey, et al., "Effect of M40403 Treatment of Diabetic Rats on Endoneurial Blood Flow, Motor Nerve Conduction Velocity and Vascular Function of Epineural Arterioles of the Siatic Nerve," British Journal of Pharmacology, Vol. 134:21-9, 2001). In patients with diabetic retinopathy serum level of lipid peroxides are higher than in healthy normals or patients with diabetes that do not have diabetic retinopathy. While levels of SOD remain the same in diabetics and normals, levels of ascorbic acid, a key antioxidant, are lower in all diabetics (Gurler, et al., "The Role of Oxidative Stress in Diabetic Retinopathy" Eye, Vol. 14:73035, 2000) The results of these studies suggest that endogenous antioxidant mechanisms are overwhelmed in patients with diabetic retinopathy.

The use of intravenously dosed Mn SOD itself to treat or prevent oxidative stress-related tissue injury in humans, such as tissue damage due to cerebral or myocardial ischemia-reperfusion injury, has been unsuccessful due to bioavailability and immunogenic issues. These problems are thought to be due to the fact that Mn SOD is a high molecular weight species. A low molecular weight compound that catalyzes superoxide disproportionation with efficiency comparable to endogenous Mn SOD would be a good candidate for minimizing the aforementioned side effects. Salvemini et. al. have disclosed a class of Mn(II)-pentaaza macrocycle complexes as low molecular weight SOD mimics. For example, in a rat model of intestinal ischemia-reperfusion, 90% of animals dosed with 1 mg/kg of compound 4 survived after 4 h, compared to 0% survival for untreated animals [Salvemini, et. al., Science, Vol. 286:304, 1999; WO 98/58636; Salvemini, et al., Drugs Future, Vol. 25(10):1027, 2000], These compounds have also been disclosed for enhancing the stability of implanted biopolymeric prosthetic devices (including ocular implants; Ornberg et. al., WO 00/72893 A2) and for the treatment of pain (Salvemini et. al., U.S. Pat. Nos. 6,180,620 B1 and 6,214,817B1).

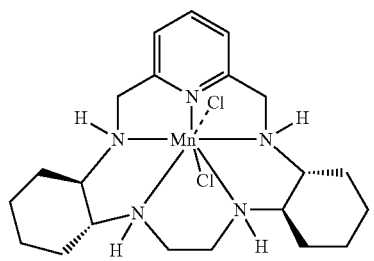

4

The use of certain Mn-salen complexes as SOD and catalase mimics with therapeutic activity has also been disclosed. For example, compound 5 has been shown to be neuroprotective in a rat stroke model (Baker et. al., J. Pharmacol. Exp. Ther., Vol. 284:215-221, 1998; Doctrow et. al., J. Med. Chem., Vol. 45:4549-4558, 2002), while compound 6 was found to increase the lifespan of mice that were deficient in endogenous expression of the enzyme superoxide dismutase 2 (Melov et. al., J. Neurosci., Vol. 21:8348-8353, 2001).

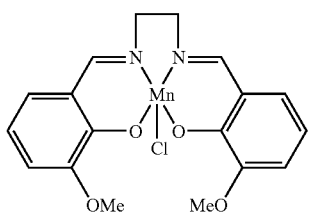

5

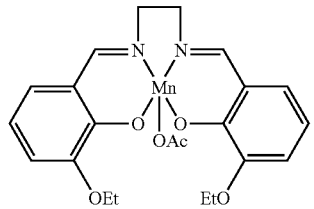

6

Other investigators have reported the use of antioxidant compounds to treat ocular diseases. Crapo et. al., have disclosed the use of porphyrin-containing SOD mimics for treating glaucoma and macular degeneration (Crapo et. al., U.S. Pat. Nos. 5,994,339 and 6,127,356). Campbell et. al. have disclosed the use of certain salen or bipyridyl Mn(II or III) phenolate complexes, including compounds I of the present invention, for treating uveitis and cataracts (Campbell et. al., U.S. Pat. Nos. 6,046,188 and 6,177,419 B1). Levin has disclosed the use of carvedilol and its derivatives and metabolites as scavengers of ROS to reduce retinal ganglion cell death (WO 00/07584 A2). Brownlee has disclosed the use of a manganese tetrakis(benzoic acid) porphyrin for reducing ROS accumulation under high glucose conditions for treating diabetic retinopathy (Brownlee, WO 00/19993 A2). The stable free radical 4-hydroxy-2,2,6,6-tetramethylpiperidine-1-oxyl, a metal-free SOD mimic, has been reported to inhibited light-induced retinal damage in albino rats (Wang et. al., Res. Commun. Mol. Pathol. Pharmacol., Vol. 89:291-305, 1995). However, in none of these reports were the compounds of the present invention disclosed or suggested for the treatment of AMD.

SUMMARY OF THE INVENTION

This application is directed to the use of mimics of the enzyme, superoxide dismutase to treat persons suffering from the exudative and non-exudative forms of AMD, diabetic retinopathy, which includes preproliferative diabetic retinopathy (collectively DR) and retinal edema.

DETAILED DESCRIPTION OF THE INVENTION

Posterior segment neovascularization is the vision-threatening pathology responsible for the two most common causes of acquired blindness in developed countries: exudative age-related macular degeneration (AMD) and proliferative diabetic retinopathy (PDR). Currently the only approved treatments for the posterior segment NV that occurs during exudative AMD are laser photocoagulation or photodynamic therapy with Visudyne®; both therapies involve occlusion of affected vasculature which results in localized laser-induced damage to the retina. Surgical interventions with vitrectomy and membrane removal are the only options currently available for patients with proliferative diabetic retinopathy. No strictly pharmacologic treatment has been approved for use against posterior segment NV, although several different compounds are being evaluated clinically, including, for example, anecortave acetate (Alcon, Inc.), EYE 001 (Eyetech), and rhuFabV2 (Genentech) for AMD and LY333531 (Lilly) and Fluocinolone (Bausch & Lomb) for diabetic macular edema.

In addition to changes in the retinal microvasculature induced by hyperglycemia in diabetic patients leading to macular edema, proliferation of neovascular membranes is also associated with vascular leakage and edema of the retina.

Where edema involves the macula, visual acuity worsens. In diabetic retinopathy, macular edema is the major cause of vision loss. Like angiogenic disorders, laser photocoagulation is used to stabilize or resolve the edematous condition. While reducing further development of edema, laser photocoagulation is a cytodestructive procedure, that, unfortunately will alter the visual field of the affected eye.

An effective pharmacologic therapy for ocular NV and edema would likely provide substantial efficacy to the patient, in many diseases thereby avoiding invasive surgical or damaging laser procedures. Effective treatment of the NV and edema would improve the patient's quality of life and productivity within society. Also, societal costs associated with providing assistance and health care to the blind could be dramatically reduced.

It has now been discovered that certain SOD mimics are useful for the treatment of AMD, DR, and retinal edema. These compounds are of formula I:

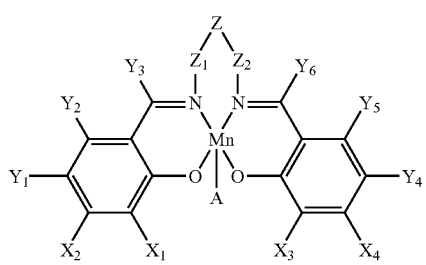

wherein:
A is a pharmaceutically acceptable anion;
$X_{1-4}$ are independently selected from the group consisting of H, halo, aryl, aralkyl, alkyl, cycloalkyl, aryloxy, free or functionally modified hydroxy, and free or functionally modified amino;
$Y_{1-6}$ are independently selected from the group consisting of H, alkyl, cycloalkyl, aryl, aralkyl, free or functionally modified hydroxy, and free or functionally modified amino; and
Z, $Z_1$, and $Z_2$ together can form a cyclohexane, pyridine, or phenyl ring; or
Z is a direct bond (i.e., $Z_1$ and $Z_2$ are bonded to each other), and $Z_1$ and $Z_2$ are each a $CH_2$ group, independently and optionally substituted with aryl, heteroaryl, alkyl, alkoxy, aralkyl, acyl, alkoxycarbonyl, or acyloxy.

Compounds I of the present invention are known, and they can be synthesized for example by the methods disclosed in U.S. Pat. No. 6,046,188, which is herein incorporated by reference.

As used herein, the term "pharmaceutically acceptable anion" means any anion that would be suitable for therapeutic administration to a patient by any conventional means without significant deleterious health consequences. Examples of preferred pharmaceutically acceptable anions include chloride, bromide, acetate, benzoate, maleate, fumarate, and succinate.

The term "free hydroxy group" means an OH. The term "functionally modified hydroxy group" means an OH which has been functionalized to form: an ether, in which an alkyl group is substituted for the hydrogen; an ester, in which an acyl group is substituted for the hydrogen; a carbamate, in which an aminocarbonyl group is substituted for the hydrogen; or a carbonate, in which an alkoxycarbonyl group is substituted for the hydrogen. Examples of preferred groups include OH, $OC(O)CH_3$, $OCH_3$, OPh, $OCH_2Ph$, and $OC(O)Ph$.

The term "free amino group" means an $NH_2$. The term "functionally modified amino group" means an $NH_2$ which has been functionalized to form: an alkoxyamino or hydroxyamino group, in which an alkoxy or hydroxy group is substituted for one of the hydrogens; an alkylamino group, in which an alkyl group is substituted for one or both of the hydrogens; an amide, in which an acyl group is substituted for one of the hydrogens; a carbamate, in which an alkoxycarbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Examples of preferred groups include $NH_2$, $NHCH_3$, $N(CH_3)_2$, NHPh, NHC(O)Ph, NHC(O)$CH_3$, NHC(O)O$CH_3$, and NHC(O)OPh.

The term "acyl" refers to a group consisting of a carbon atom that has a double bond to an oxygen atom and a single bond to another atom. Preferred acyl groups include acetyl, propionyl, butyryl, and pentanoyl.

The term "acyloxy" represents a unit consisting of an acyl group that is bonded to an oxygen atom. Examples of preferred acyloxy groups include $CH_3C(O)O$, $C_2H_5C(O)O$, n-$C_3H_7C(O)O$, and n-$C_4H_9C(O)O$.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, alkoxy, or lower alkyl. Preferred cycloalkyl groups include cyclopropyl, cyclobutyl, cyclopentyl and cyclohexyl.

The term "alkoxy" represents an alkyl group attached through an oxygen linkage.

The term "carbonyl group" represents a carbon atom double bonded to an oxygen atom, wherein the carbon atom has two free valencies.

The term "alkoxycarbonyl" represents a unit consisting of an alkoxy group bonded from its oxygen atom to the carbon of a carbonyl group.

The term "aminocarbonyl" represents a moiety consisting of an amino group bonded from its nitrogen atom to the carbon atom of a carbonyl group.

The term "lower alkyl" represents alkyl groups containing one to six carbons ($C_1$-$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "aryloxy" represents an aryl group bonded to an oxygen atom.

The term "aralkyl" represents an aryl group bonded to an alkyl group.

Preferred compounds of the present invention include those of formula I, wherein:
A is chloride, bromide, or acetate;
$X_{1-4}$ are independently H, fluoro, bromo, chloro, alkyl, or a free or functionally modified hydroxy or amino group;
$Y_{1-4}$ are independently H, alkyl, or a free or functionally modified hydroxy; and
Z, $Z_1$, and $Z_2$ together form a cyclohexane, pyridine, or phenyl ring, or
Z is a direct bond, and $Z_1$ and $Z_2$ are each a $CH_2$ group, either unsubstituted or substituted with phenyl, benzyloxy, or an acyloxy group.

Among the especially preferred compounds of formula I are the 5-7 below:

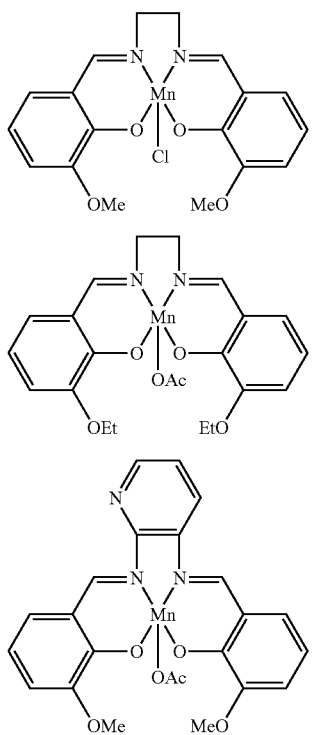

The present invention is also directed to the provision of compositions adapted for treatment of retinal and optic nerve head tissues. The ophthalmic compositions of the present invention will include one or more SOD mimics and a pharmaceutically acceptable vehicle. Various types of vehicles may be used. The vehicles will generally be aqueous in nature. Aqueous solutions are generally preferred, based on ease of formulation, as well as a patient's ability to easily administer such compositions by means of instilling one to two drops of the solutions in the affected eyes. However, the SOD mimics of the present invention may also be readily incorporated into other types of compositions, such as suspensions, viscous or semi-viscous gels, or other types of solid or semi-solid compositions. Suspensions may be preferred for SOD mimics that are relatively insoluble in water. The ophthalmic compositions of the present invention may also include various other ingredients, such as buffers, preservatives, co-solvents, and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

The route of administration (e.g., topical, ocular injection, parenteral, or oral) and the dosage regimen will be determined by skilled clinicians, based on factors such as the exact nature of the condition being treated, the severity of the condition, and the age and general physical condition of the patient.

In general, the doses used for the above described purposes will vary, but will be in an effective amount to prevent or treat AMD, DR, and retinal edema. As used herein, the term "pharmaceutically effective amount" refers to an amount of one or more SOD mimics which will effectively treat AMD, DR, and/or retinal edema in a human patient. The doses used for any of the above-described purposes will generally be from about 0.01 to about 100 milligrams per kilogram of body weight (mg/kg), administered one to four times per day. When the compositions are dosed topically, they will generally be in a concentration range of from 0.001 to about 5% w/v, with 1-2 drops administered 1-4 times per day.

As used herein, the term "pharmaceutically acceptable carrier" refers to any formulation that is safe, and provides the appropriate delivery for the desired route of administration of an effective amount of at least one compound of the present invention.

The following Examples 1 and 2 are formulations useful for intraocular, periocular, or retrobulbar injection or perfusion.

EXAMPLE 1

| Component | % w/v |
| --- | --- |
| Compound of formula I | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |

EXAMPLE 2

| Component | % w/v |
| --- | --- |
| Compound of formula I | 0.1 |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

EXAMPLE 3

The following tablet formulation can be made pursuant to U.S. Pat. No. 5,049,586, incorporated herein by reference.

| Component | % w/v |
| --- | --- |
| Compound of formula I | 60 |
| Magnesium oxide | 20 |
| Corn starch | 15 |
| Polyvinylpyrrolidone | 3 |
| Sodium carboxymethylcellulose | 1 |
| Magnesium stearate | 0.8 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method for treating AMD, DR, and/or retinal edema in a patient which comprises administering to the patient in need of such treatment a pharmaceutical composition formulated for intraocular, periocular, or retrobulbar injection or perfusion, wherein the composition comprises a pharmaceutically effective amount of a compound of formula I:

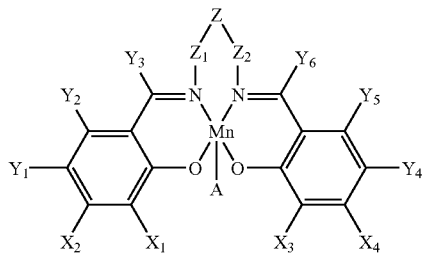

wherein:
A is a pharmaceutically acceptable anion;
$X_{1-4}$ are independently selected from the group consisting of H, halo, aryl, aralkyl, alkyl, cycloalkyl, aryloxy, free or functionally modified hydroxy, and free or functionally modified amino;
$Y_{1-6}$ are independently selected from the group consisting of H, alkyl, cycloalkyl, aryl, aralkyl, free or functionally modified hydroxy, and free or functionally modified amino; and
Z, $Z_1$, and $Z_2$ together can form a cyclohexane, pyridine, or phenyl ring; or
Z is a direct bond, and $Z_1$ and $Z_2$ are each a $CH_2$ group, independently and optionally substituted with aryl, heteroaryl, alkyl, alkoxy, aralkyl, acyl, alkoxycarbonyl, or acyloxy.

2. The method of claim 1, wherein for the compound of formula I:
A is chloride, bromide, or acetate;
$X_{1-4}$ are independently H, fluoro, bromo, chloro, alkyl, or a free or functionally modified hydroxy or amino group;
$Y_{1-4}$ are independently H, alkyl, or a free or functionally modified hydroxy; and
Z, $Z_1$, and $Z_2$ together form a cyclohexane, pyridine, or phenyl ring, or
Z is a direct bond, and $Z_1$ and $Z_2$ are each a $CH_2$ group, either unsubstituted or substituted with phenyl, benzyloxy, or an acyloxy group.

3. The method of claim 1, wherein the compound is selected from the group consisting of:

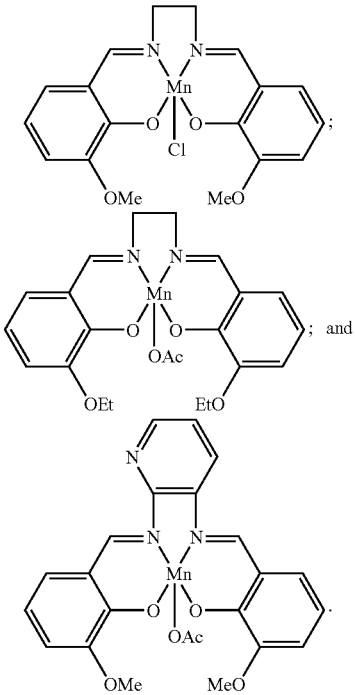

4. The method of claim 1, wherein the pharmaceutical composition further comprises diabasic sodium phosphate, hydroxypropyl methylcellulose (HPMC), polysorbate 80, and benzalkonium chloride.

5. The method of claim 4, wherein the pharmaceutical composition further comprises sodium chloride, edentate disodium, and has a pH of 7.4.

* * * * *